United States Patent [19]

Scherrer et al.

[11] 4,153,716

[45] May 8, 1979

[54] OXY, THIO, SULFENYL AND SULFONYL DERIVATIVES OF 2-NITRO-3-PHENYLBENZOFURAN

[75] Inventors: Robert A. Scherrer, White Bear Lake; Walton J. Hammar, St. Paul; Richard M. Stern, Cottage Grove, all of Minn.

[73] Assignee: Riker Laboratories, Inc., Northridge, Calif.

[21] Appl. No.: 862,015

[22] Filed: Dec. 19, 1977

[51] Int. Cl.$^2$ .................. A61K 31/345; C07D 307/82
[52] U.S. Cl. ..................... 424/274; 424/285; 260/326.55 F; 260/346.22; 260/346.73
[58] Field of Search ...................... 260/346.22, 346.73, 260/326.5 SF; 424/274, 285

[56] References Cited

U.S. PATENT DOCUMENTS

| 3,808,236 | 4/1974 | Royer et al. | 260/346.22 |
| 4,048,323 | 9/1977 | Scherrer | 260/346.22 |
| 4,066,782 | 1/1978 | Scherrer | 260/346.22 |
| 4,067,993 | 1/1978 | Scherrer | 260/346.22 |

OTHER PUBLICATIONS

Royer et al., Chimie Therapeutique 1973, No. 2, pp. 139–142.

Primary Examiner—Natalie Trousof
Assistant Examiner—Bernard Dentz
Attorney, Agent, or Firm—Cruzan Alexander; Donald M. Sell; Donald C. Gipple

[57] ABSTRACT

Compounds wherein 2-nitro-3-phenylbenzofuran is substituted by one or two alcohol or thioalcohol-containing functional groups, or derivatives thereof, are active as antimicrobial agents.

15 Claims, No Drawings

OXY, THIO, SULFENYL AND SULFONYL DERIVATIVES OF 2-NITRO-3-PHENYLBENZOFURAN

BACKGROUND OF THE INVENTION

This invention relates to a class of 2-nitro-3-phenylbenzofuran compounds which are substituted on the 3-phenyl and/or the benzo ring by an alcohol or thioalcohol-containing functional group or a derivative thereof, and to the use of these compounds as antimicrobial agents.

Certain neutral 2-nitrobenzofurans are known as antibacterial agents, for example, see French Pat. No. 2,081,585 and several publications by Rene Royer, et al. In addition, compounds wherein 2-nitro-3-phenylbenzofuran is substituted by an alkanoic acid group are known to have antimicrobial activity (see Belgian Pat. No. 846,502 and German Offenlegungsschrift P No. 2642877). However, compounds wherein 2-nitro-3-phenylbenzofuran is substituted by an alcohol or thioalcohol-containing functional group have not previously been reported.

DETAILED DESCRIPTION OF THE INVENTION

The present invention relates to compounds wherein 2-nitro-3-phenylbenzofuran is substituted by one or two alcohol or thioalcohol-containing functional groups, and derivatives thereof. It also relates to use of the compounds as antimicrobial agents and to synthetic intermediates useful for the preparation of compounds of the invention.

According to the present invention there is provided a class of compounds of the formula

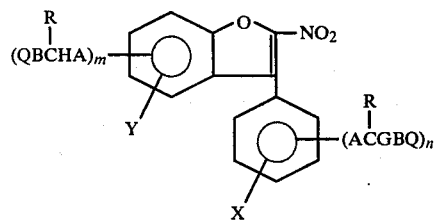

wherein
A is a carbon-carbon bond, methylene,

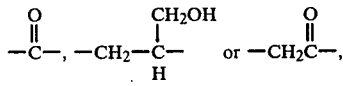

R is hydrogen, alkyl of one to ten carbon atoms or cyano,
B is oxygen, sulfur, sulfinyl or sulfonyl,
Q is hydrogen, amino, methylamino, N-bonded pyrrolidinyl, alkyl of one to four carbon atoms,

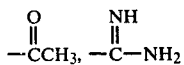

or nitroso,
X is hydrogen, methyl, fluorine, chlorine or bromine and
Y is hydrogen, methyl or ethyl, provided that when Q is amino (—NH₂), methylamino or pyrrolidinyl, B and R in the same moiety are respectively sulfonyl and hydrogen.

The moieties

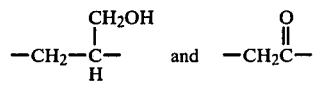

are shown in the foregoing (as possible variations of A) in such a way that the left hand side of each is bonded to the ring.

The pure compounds of the invention are generally yellow or yellowish solids. They are substantially insoluble in water or aliphatic hydrocarbons and are more soluble in acetone, lower alcohols, benzene, N,N-dimethylformamide and the like. All of the compounds of the invention are active against bacteria and some are also active against other microorganisms, including fungi and protozoa, in vitro and topically. Thus, they can be used for disinfecting and sterilizing, for example of medical and dental equipment, as components of disinfecting solutions. The compounds are particularly useful as antibacterial agents. In general, the compounds are also active in vivo in animals.

The compounds of the invention wherein Q contains zero, one or two carbon atoms are presently preferred. It is also preferred that X and R are hydrogen. When A is

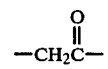

or carbonyl, it is preferred that R and Q are both hydrogens and B is oxygen. Other preferred subclasses are the compounds in which B is sulfur, sulfinyl or sulfonyl and R is hydrogen and in which R is cyano, B is oxygen and Q is hydrogen. However, when B is oxygen, Q is preferably not

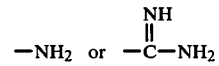

and when B is sulfur, sulfinyl or sulfonyl, Q is preferably not nitroso or acetyl.

The compounds of the invention are prepared by several methods from starting materials which are known to the art or which are prepared by methods known to those skilled in the art.

The compounds of the invention in which the moiety

is hydroxymethyl or hydroxyethyl can be prepared by reduction of the corresponding known aldehydes, carboxylic acids or acetic acids or their esters. Such reductions are carried out using hydride reducing agents such as sodium borohydride (primarily for aldehydes or esters), lithium aluminum hydride or borane. The reductions can be carried out either before or after the benzofuran ring has been substituted by the 2-nitro group, except when lithium aluminum hydride is used.

The compounds wherein A is

or carbonyl can be prepared from the corresponding acids. When B is oxygen and R and Q are hydrogen, the acid is converted by known methods using e.g. thionyl chloride, to the acid chloride, then to the diazomethyl ketone and finally hydrolyzed to the desired product, which may be called a hydroxymethyl ketone. Alternatively, the hydrolysis can be carried out with hydrogen sulfide to yield a product wherein B is sulfur.

In order to prepare the compounds in which B is sulfur, the corresponding bromo or bromoalkyl derivatives are reacted with various nucleophilic thio compounds such as alkyl mercaptans, dimethyl sulfide, thioguanidine and the like. The corresponding sulfinyl or sulfonyl compounds can then be prepared by mild oxidation of the compounds in which B is sulfur with hydrogen peroxide or peracids, or other generally used methods can be used.

In order to prepare compounds wherein B is sulfonyl and Q is $NH_2$, the corresponding bromo compound is reacted with thiourea to yield the thio compound, followed by oxidative chlorination to give the sulfonyl chloride compound. That compound reacts readily with ammonia to give the corresponding sulfonamide. The corresponding compounds in which Q is methylamino and N-bonded pyrrolidinyl can be prepared by reacting the sulfonyl chloride with methylamine and pyrrolidine instead of ammonia.

In order to prepare compounds wherein Q is acetyl, simple reaction of the corresponding thio or hydroxy compound with acetyl chloride may be carried out. Other common reactions of thioalcohols and alcohols can be used to derivatize thioalcohol and alcohol compounds of the invention.

In order to prepare compounds of the invention wherein R is cyano and B-Q is hydroxy, the corresponding aldehyde is reacted with an alkali metal cyanide in the manner known to the art.

In order to prepare compounds of the invention wherein A is

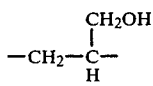

(written so that the left side of the moiety is bonded to the ring), a known 2-nitro-3-phenylbenzofuranylaldehyde is reacted with a dialkyl (e.g. diethyl) malonate by heating in an inert solvent such as benzene or toluene at the reflux temperature of the reaction mixture. This reaction is carried out in the presence of a weak organic (e.g. piperidine) or inorganic (e.g. sodium or potassium carbonate) base. The double bond resulting from the condensation is reduced by conventional methods such as sodium borohydride reduction in an ethanol-glyme mixture at about 0° to 50° C.

When the hydroxyethyl-2-bromo-3-phenylbenzofuran intermediates are reacted with excess dinitrogen tetraoxide in the presence of a hydrogen bromide scavenger such as 4-cyclohexenecarboxylic acid to provide the desired 2-nitro compound, it is also possible to isolate the corresponding nitrite ester. If one wishes more nitrite ester, a larger excess of dinitrogen tetraoxide is used.

Grignard reagents of bromosubstituted-3-phenylbenzofurans can be formed using standard methods and reacted with alkanaldehydes to provide α-hydroxyalkyl-substituted compounds of the invention.

It has been found that hydroxyalkyl-substituted compounds of the invention will react with phosphorus tribromide to provide the corresponding bromoalkyl-substituted compounds. When such bromoalkyl compounds are heated at reflux in ethanol with proline, the ethoxyalkyl-substituted compounds are obtained.

The nitration of the 2 position of the compounds of the invention is accomplished, starting with corresponding 2-halo (e.g. bromo) or 2-unsubstituted compounds using methods analogous to those of the prior art, e.g. see U.S. Pat. No. 4,048,323. In some preparations, the nitration of the 2 position is the final step in the synthesis and in others it is accomplished in an earlier step.

The alkyl and halogen substituents on the aromatic rings of the compounds of the invention (X and Y) are conveniently brought forward from starting materials bearing such substituents, although this is not necessarily the case.

The antimicrobial activity of the compounds is evaluated using a variation of the original agar-plate diffusion method of Vincent and Vincent (e.g. see Vincent, J. G., and Vincent, Helen W., Proc. Soc. Exptl. Biol. Med. 55:162–164, 1944, and Davis, B. D., and Mingioli, E. S., J. Bac. 66:129–136, 1953). Using this test, the compounds of the invention have been found to have a broad spectrum of activity against both gram-positive and gram-negative microorganisms. The procedure provides information on the amount of a compound required to give complete inhibition, partial inhibition or no inhibition of microbial growth on agar plates. The microbial growth on each plate is read visually, and minimal inhibitory concentrations are recorded.

The microorganisms used are: *Staphylococcus aureus, Bacillus subtilus, Pseudomonas aeruginosa, Escherichi coli, Streptosoccus sp.* (strains isolated from dental caries in rats or hamsters at the National Institute of Dental Health and grown in PFY or APT agar), *Asperigillus niger, Candida albicans, Mima polymorpha, Herellea vaginicola, Klebsiella pneumoniae* and *Streptococcus fecaelis.*

These are selected representatives of various bacterial and fungal classes and broad spectrum activity can be predicted as a result of activity against them. All of the compounds of the invention possess antimicrobial activity towards one or more of the above microorganisms. The compounds maintain high activity against the microorganisms either in the absence or presence of ten percent horse serum.

The in vivo antimicrobial activity is determined against infections produced by *Streptococcus pyogenes* C-203 and *Staphylococcus* aureus (Smith) or other bacterial species. The species used is determined by the in vitro antimicrobial spectrum of the compound. Groups of five or ten mice, 18–22 g., are infected intraperitoneally with the test culture. Treatment consists of three oral injections one, six and twenty-four hours after infection. All mice are observed for extended periods, e.g. for two weeks, and deaths recorded at daily intervals. Control groups consist of one infected, nontreated group and other infected groups receiving varying dosages of the reference standard.

The acute oral toxicity of the compounds of the invention generally is moderate to low compared with the effective oral dose, and they have a good to excellent therapeutic ratio.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and for formulation is used by immersing the object to be treated therein, or by local application to an infected area. The amount of compound to be used for treatment (e.g. oral treatment) of a microbial infection will be an effective amount less than a toxic amount. The amount to be administered to a subject and route of administration to control an infection will depend on the species of organism, the sex, weight, physical condition of the subject, the locus of the infection, and many other factors, but this judgement is well within the skill of the art. Usually the amount will be less than 100 mg/kg per dose. Conveniently the oral treatment is administered in the form of the usual pharmaceutical preparations such as capsules, tablets, emulsions, solutions, suppositories and the like. Excipients, fillers, coatings, etc. are employed with tablets or capsules, as is well known in the art. It is often advantageous to combine the compounds of this invention with other antimicrobial compounds such as coccidiostats, anthelmintics, antifungals, antibiotics, steroids or antibacterial agents, or to combine more than one compound described herein in a single composition.

Certain of the compounds are also active antiparasitics as shown by activity in laboratory tests versus the protozoan Trichomonas sp. In view of the outstanding antimocrobial activity of the compounds, they would also be expected to be effective growth promoters in various animal and bird species.

The following examples are given for the purpose of further illustrating the procedures of the present invention, but are not intended, in any way, to be limiting on the scope thereof. The melting points are uncorrected, the temperatures are in degrees Centigrade and the pressures in millimeters of mercury.

EXAMPLE 1

Step A. Methyl 4-hydroxyphenylacetate is condensed with 4-bromo-α-bromoacetophenone by refluxing in glyme in the presence of potassium carbonate. The product is cyclized by heating in polyphosphoric acid to provide methyl 3-(4-bromophenyl)-benzofuran-5-acetate (m.p. 84°–86° C.).

A stirred mixture of 40 g. of cuprous cyanide and 99 g. (0.29 mole) of methyl 3-(4-bromophenyl)benzofuran-5-acetate in 30 ml. of pyridine is heated at 160°–175° C. under a nitrogen atmosphere for 20 hours, cooled to about 100° C., and then a solution of 200 g. of ferric chloride, 100 ml. of concentrated hydrochloric acid and 200 ml. of ice water is added. To this mixture is added 300 ml. of chloroform, and stirring is continued for one hour. The solid is separated by filtration and washed with chloroform. The filtrate and washings are combined, dried, then evaporated to provide a residue which is recrystallized from an N,N-dimethylformamide-water mixture to provide methyl 3-(4-cyanophenyl)-benzofuran-5-acetate.

Step B. To a suspension of 5 g. of the product of step A in 20 ml. of ethanol is added 50 ml. of 30 percent sodium hydroxide solution, and the mixture is refluxed for 30 minutes, 75 ml. of water is added, and the mixture is refluxed for an additional three hours. The mixture is decanted into 125 ml. of 6N hydrochloric acid, the solid is separated by filtration then recrystallized from acetic acid to provide 3-(4-carboxyphenyl)benzofuran-5-acetic acid, m.p. 278°–281° C.

Step C. To a suspension of 2 g. of the product of step B in 10 ml. of acetonitrile is added 0.2 g. of cupric nitrate followed by 1 g. of dinitrogen tetraoxide in 2 ml. of acetonitrile. After stirring for two hours an additional 0.5 g. of dinitrogen tetraoxide is added, and stirring is continued for 18 hours. Evaporation provides a solid residue which is recrystallized from acetic acid yielding yellow crystals of 2-nitro-3-(4-carboxyphenyl)benzofuran-5-acetic acid, m.p. 290° C. (dec.).

Step D. A solution of 1 g. of the product of step C in 25 ml. of tetrahydrofuran is treated with 20 ml. of 1N diborane for one hour at room temperature, then heated for 15 minutes on a steam bath. To the solution is added 10 ml. of 6N hydrochloric acid, and heating is continued on the steam bath for 30 minutes while evaporating to 15 ml. total volume. The solution is made basic with 10 percent sodium hydroxide solution, extracted with chloroform, and the extracts are dried, then evaporated. The residue is recrystallized from chloroform to provide yellow crystals of 5-(2-hydroxyethyl)-2-nitro-3-(4-hydroxymethylphenyl)benzofuran, m.p. 135°–137° C.

| Analysis: | % C | % H | % N |
|---|---|---|---|
| Calculated for $C_{17}H_{15}NO_5 \cdot \frac{1}{2} H_2O$: | 63.3; | 4.9; | 4.3 |
| Found: | 62.8; | 4.6; | 4.2. |

EXAMPLE 2

Using the method of step D, Example 1, methyl 3-(4-bromophenyl)benzofuran-5-acetate (preparation shown in step A of Example 1) is reduced to provide 3-(4-bromophenyl)-5-(2-hydroxyethyl)benzofuran.

Using the method of step C, Example 1, 3-(4-bromophenyl)-5-(2-hydroxyethyl)benzofuran is nitrated to provide 3-(4-bromophenyl)-5-(2-hydroxyethyl)-2-nitrobenzofuran.

EXAMPLE 3

Step A. A stirred mixture of 5.7 g. (0.0355 mole) of diethyl malonate, 10 g. (0.0375 mole) of 2-nitro-3-phenyl-7-benzofuranaldehyde (described in Belgian Pat. No. 846,502, Example 13), 0.15 g. of 2-nitro-3-phenyl-7-benzofurancarboxylic acid and 0.2 ml. of piperidine in 30 ml. of benzene is heated at its reflux temperature for about nine hours. The mixture is treated with 100 ml. of benzene and 100 ml. of water, the benzene layer is separated, washed with water, twice with 1N hydrochloric acid then with 100 ml. of sodium bicarbonate solution and dried. Evaporation provides a residue which is recrystallized from a cyclohexanebenzene mixture to provide yellow crystals of diethyl 2-nitro-3-phenyl-7-benzofuranylmethylenemalonate, m.p. 139°–140.5° C.

Step B. To 0.76 g. of sodium borohydride in 50 ml. of ethanol and 30 ml. of glyme is added 8.0 g. (0.020 mole) of the product of step A in 100 ml. of glyme at 0° to 5° C. The mixture is stirred at 5° C. for one hour and stirring is continued as the temperature rises to 20° C. over 2.5 hours. Addition of 800 ml. of water, followed by extraction with diethyl ether, drying and evaporation provides a residue which is recrystallized from trichloroethylene, then ethanol, then benzene to provide 2-(2-nitro-3-phenyl-7-benzofuranylmethyl)-1,3-propanediol as a yellow residue, m.p. 166°–168° C. Spectral analysis by mass spectra, nuclear magnetic resonance and infrared supports the structural assignment.

EXAMPLE 4

Using the method of Example 3 and starting with 3-(4-methylphenyl)-2-nitrobenzofuran-5-aldehyde (prepared from 5-bromo-3-phenylbenzofuran according to the method of Belgium Pat. No. 846,502, Example 13) one obtains 2-[3-(4-methylphenyl)-2-nitro-5-benzofuranylmethyl]-1,3-propanediol.

EXAMPLE 5

Step A. Ethyl 3-phenyl-7-benzofuranacetate (U.S. Pat. No. 4,013,692, Example 17) is reacted according to the process of Example 12 of the present specification to form 7-(2-hydroxyethyl)-3-phenylbenzofuran.

To a solution of 3.0 g. (0.0126 mole) of 7-(2-hydroxyethyl)-3-phenylbenzofuran in 50 ml. of dichloromethane is added dropwise 2.1 g. of bromine. After stirring for five minutes the mixture is evaporated, benzene is added to the residue and it is evaporated again. The residue is mixed with petroleum ether and crystallizes. Recrystallization from hexane gives 2-bromo-7-(2-hydroxyethyl)-3-phenylbenzofuran, m.p. 108°–112° C.

Step B. The product of step A and 2 g. of 4-cyclohexenecarboxylic acid are dissolved in 25 ml. of acetic acid, and 1.8 g. of dinitrogen tetraoxide in 5 ml. of acetic acid are added dropwise. After stirring 20 minutes at room temperature, the mixture is heated at 45° C. for one hour, then at 55° C. for one hour. The mixture is then partially evaporated to remove residual dinitrogen tetraoxide, poured into water, then extracted with diethyl ether. The ether extracts are washed thrice with water, twice with sodium bicarbonate solution, once with water, and dried. Evaporation provides a residue which is dissolved in hexane-chloroform and fractionated by chromatography on silica gel, using hexane-chloroform as eluent. Thin layer chromatographic analysis determines that two relatively pure components are obtained. Recrystallization of the first main component twice from a hexanebenzene mixture provides yellow flakes of 2-(2-nitro-3-phenyl-7-benzofuranyl)ethyl acetate, m.p. 95°–98° C.

| Analysis: | % C | % H | % N |
|---|---|---|---|
| Calculated for $C_{18}H_{15}NO_5$: | 66.5; | 4.6; | 4.3 |
| Found: | 66.2; | 4.6; | 4.3. |

Recrystallization of the second main component twice from carbon tetrachloride provides 7-(2-hydroxyethyl)-2-nitro-3-phenylbenzofuran, m.p. 133°–136° C.

| Analysis: | % C | % H | % N |
|---|---|---|---|
| Calculated for $C_{16}H_{13}NO_4$: | 67.9; | 4.6; | 5.0 |
| Found: | 67.3; | 4.5; | 5.0. |

EXAMPLE 6

To a stirred mixture of 28.6 g. (0.0904 mole) of 2-bromo-7-(2-hydroxyethyl)-3-phenylbenzofuran (the product of step A, Example 5) and 15.1 g. of 4-cyclohexenecarboxylic acid in 250 ml. of chloroform is added dropwise 10.8 g. (0.118 mole) of dinitrogen tetraoxide in 30 ml. of chloroform. After 16 hours, 7 g. of dinitrogen tetraoxide and 5 g. of 4-cyclohexenecarboxylic acid in 30 ml. of chloroform are added, and the mixture is heated at 45° C. for four hours. Water is added to the mixture, the chloroform layer is separated and washed with water, then thrice with sodium bicarbonate solution, thrice with water, once with saturated sodium chloride solution and dried. Evaporation provides a yellow residue. Thin layer chromatographic analysis shows two main products. This residue is recrystallized from 50/50 ethanol/water, then again from carbon tetrachloride to yield 7-(2-hydroxyethyl)-2-nitro-3-phenylbenzofuran as a yellow solid, m.p. 133.5°–136° C.

| Analysis: | % C | % H | % N |
|---|---|---|---|
| Calculated for $C_{16}H_{13}NO_4$: | 67.9; | 4.6; | 5.0 |
| Found: | 67.3; | 4.5; | 5.0. |

When this residue is recrystallized from cyclohexane the other product is obtained. Two more recrystallizations from cyclohexane and one from a benzene cyclohexane mixture provides 3-(2-nitro-3-phenyl-7-benzofuranyl)ethyl nitrite, m.p. 103°–105.5° C.

| Analysis: | % C | % H | % N |
|---|---|---|---|
| Calculated for $C_{16}H_{12}N_2O_5 \cdot 12\%$ cyclohexane: | 62.3; | 4.2; | 8.6 |
| Found: | 62.3; | 4.1; | 8.3. |

Infrared spectral analysis supports the structural assignment.

EXAMPLE 7

To a stirred mixture of 0.11 g. of sodium borohydride in 5 ml. of glyme is added dropwise 1.7 g. (0.0064 mole) of 2-nitro-3-phenyl-7-benzofuranaldehyde in 45 ml. of glyme. After 30 minutes, a small portion of 10 percent sodium hydroxide solution is added, then 20 ml. of water, then enough 6N hydrochloric acid to acidify the mixture. The mixture is then extracted with dichloromethane, the extracts are washed twice with water and dried. Evaporation provides a residue which solidifies. Recrystallization twice from a benzene-hexane mixture provides yellow 7-hydroxymethyl-2-nitro-3-phenylbenzofuran, m.p. 128.5°–130° C.

| Analysis: | % C | % H | % N |
|---|---|---|---|
| Calculated for $C_{15}H_{11}NO_4$: | 67.0; | 4.1; | 5.2 |
| Found: | 67.5; | 4.1; | 5.1. |

EXAMPLE 8

Starting with 3-(4-cyanophenyl)benzofuran (described in U.S. Pat. No. 4,048,323, Example 1) and reducing with Raney nickel alloy, one obtains 4-(3-benzofuranyl)benzaldehyde. This product is reacted according to the method of Example 1, step C, hereof to provide 4-(2-nitro-3-benzofuranyl)benzaldehyde which is reduced using the method of Example 7 to provide 3-(4-hydroxymethylphenyl)-2-nitrobenzofuran.

EXAMPLE 9

Step A. To 70 ml. of a diethyl ether solution of 1.05 g. (0.025 mole) of diazomethane is added dropwise 3.2 g. (0.01 mole) of 2-nitro-3-phenylbenzofuran-5-acetyl chloride (described in Belgian Pat. No. 846,502, Example 15). After stirring for two hours, the solution is evaporated to provide yellow solid 5-(2-nitro-3-phenylbenzofuranyl)methyl diazomethyl ketone. The structure assignment is supported by infrared spectral analysis.

Step B. The product of step A is dissolved in 60 ml. of acetonitrile, 30 ml. of 0.5N perchloric acid is added, and the mixture is heated at 65° C. for 30 minutes. Evaporation to remove acetonitrile is followed by addition of water and complete evaporation. The residue is dissolved in diethyl ether, the solution is washed with water, then saturated sodium chloride solution and dried. Evaporation provides a yellow solid which is dissolved in chloroform and eluted through a silica gel column with chloroform. Later fractions are evaporated to provide a yellow solid which is recrystallized from an ethyl acetate-petroleum ether mixture to 1-hydroxy-3-(2-nitro-3-phenyl-5-benzofuranyl)-2-propanone, m.p. 148°–151° C. (dec.).

| Analysis: | % C | % H | % N |
|---|---|---|---|
| Calculated for $C_{17}H_{13}NO_5$: | 65.6; | 4.2; | 4.5 |
| Found: | 65.4; | 4.2; | 4.5. |

EXAMPLE 10

Step A. Using the method of Example 9A, 2-nitro-3-phenylbenzofuran-5-carboxyl chloride (prepared by reacting the corresponding acid shown in German Offenlegungsschrift P 26 42 877, Example 7, with thionyl chloride) is reacted with diazomethane to provide yellow solid 5-(2-nitro-3-phenylbenzofuranyl)methyl diazomethyl ketone. The structural assignment is supported by infrared spectral analysis.

Step B. The product of step A is converted using the method of Example 9B hereof to hydroxymethyl 2-nitro-3-phenyl-5-benzofuranyl ketone, m.p. 170°–176° C.

| Analysis: | % C | % H | % N |
|---|---|---|---|
| Calculated for $C_{16}H_{11}NO_5$: | 64.6; | 3.73; | 4.71 |
| Found: | 64.7; | 3.9; | 4.7. |

EXAMPLE 11

Step A. To a solution of 5.5 g. (0.02 mole) of 5-bromo-3-phenylbenzofuran in tetrahydrofuran is added 0.5 g. (0.02 mole) of magnesium, and the mixture is heated at its reflux temperature for three hours. After cooling to 0° C., 3.4 g. of undecyl aldehyde is added. After stirring for 30 minutes at room temperature, the solution is added to ammonium chloride solution. Evaporation provides a residue which is mixed with diethyl ether and water. The ether layer is separated, washed with saturated sodium chloride solution, dried and evaporated. The resulting oil is dissolved in carbon tetrachloride and eluted from a silica gel column with carbon tetrachloride, then with dichloromethane. The later fractions are evaporated to provide 5-(α-hydroxyundecyl)-3-phenylbenzofuran which is dissolved in dichloromethane.

Step B. To the solution of product from step A is added 2 g. of dinitrogen tetraoxide dissolved in dichloromethane, and the mixture is stirred for about 16 hours. Evaporation provides a residue which is mixed with ice and 10 percent sodium hydroxide solution. The mixture is stirred for 15 minutes, then cold 6N hydrochloric acid and diethyl ether are added. The ether layer is separated, then washed with saturated sodium chloride solution and dried. The solution is chromatographed on silica gel, eluting first with carbon tetrachloride, then dichloromethane. The later fractions are evaporated to provide 1-(2-nitro-3-phenyl-5-benzofuranyl)undecan-1-ol as a yellow solid, m.p. 84°–85° C. after recrystallization from hexane.

| Analysis: | % C | % H | % N |
|---|---|---|---|
| Calculated for $C_{25}H_{31}NO_4$: | 73.3; | 7.6; | 3.4 |
| Found: | 73.6; | 7.7; | 3.2. |

EXAMPLE 12

Step A. To a mixture of 200 ml. of diethyl ether and 3.8 g. (0.1 mole) of lithium aluminum hydride under nitrogen is added dropwise a solution of 16 g. (0.057 mole) of ethyl 3-phenylbenzofuran-5-acetate (prepared from ethyl 4-hydroxyphenyl acetate and α-bromoacetophenone by the method described in Belgian Pat. No. 846,502) in 70 ml. of ether at a rate sufficient to maintain reflux for a total of one hour. The reaction is terminated by cautiously adding water (a total of 100 ml.). A 65 ml. portion of 10 percent sulfuric acid is added, the layers are separated and the organic layer is washed twice with water, twice with saturated sodium chloride solution and dried. Evaporation to dryness provides an orange residue of 5-(2-hydroxyethyl)-3-phenylbenzofuran. The structural assignment is confirmed by infrared and nuclear magnetic resonance spectral analysis.

Step B. The product from step A is dissolved in 200 ml. of dichloromethane, the solution is cooled to 5° C., and 9.16 g. (0.0573 mole) of bromine in 50 ml. of dichloromethane is added dropwise. The solution is allowed to warm to 15° C., then evaporated to provide a green residue of 2-bromo-5-(2-hydroxyethyl)-3-phenylbenzofuran. The structural assignment is confirmed by infrared and nuclear magnetic resonance spectral analysis.

Step C. The product from step B is mixed with 8.83 g. (0.07 mole) of cyclohexene-4-carboxylic acid in 175 ml. of chloroform, and 6.5 g. (0.07 mole) of dinitrogen tetraoxide in 15 ml. of chloroform is added dropwise. After 30 minutes an additional 1.0 g. of dinitrogen tetraoxide in 5 ml. of chloroform is added, and the mixture is stirred for about 18 hours. The mixture is washed twice with water, twice with saturated sodium bicarbonate solution and twice again with water, then dried. Evaporation to dryness provides a residue which is recrystallized from aqueous ethanol, then benzene, to provide 5-(2-hydroxyethyl)-2-nitro-3-phenylbenzofuran as a yellow solid, m.p. 169°–173° C.

| Analysis: | % C | % H | % N |
|---|---|---|---|
| Calculated for $C_{16}H_{13}NO_4$: | 67.8; | 4.6; | 4.9 |
| Found: | 67.5; | 4.5; | 4.7. |

EXAMPLE 13

A mixture of 1.04 g. (0.009 mole) of proline and 3 g. (0.009 mole) of 5-(2-bromoethyl)-2-nitro-3-phenylbenzofuran (prepared by reaction of 5-(2-hydroxyethyl)-2-nitro-3-phenylbenzofuran with phosphorus tribromide) in 50 ml. of ethanol is heated to its reflux temperature and maintained at reflux temperature for about 14 hours. The mixture is evaporated to provide a solid residue which is recrystallized from ethanol to provide 5-ethoxyethyl-2-nitro-3-phenylbenzofuran, m.p. 108°–109° C.

| Analysis: | % C | % H | % N |
| --- | --- | --- | --- |
| Calculated for $C_{17}H_{15}NO_4$: | 68.7; | 5.0; | 4.7 |
| Found: | 68.3; | 4.9; | 4.7. |

EXAMPLE 14

A stirred solution of 3.0 g. (0.0106 mole) of 2-nitro-3-phenylbenzofuran-5-carboxylic acid in 50 ml. of tetrahydrofuran is treated with 25 ml. (0.025 mole) of 1M borane in tetrahydrofuran. After 16 hours at about 20° C., 40 ml. of 3N sulfuric acid is added gradually, then the mixture is refluxed for 45 minutes. The mixture is evaporated to remove tetrahydrofuran, then filtered to separate the solid 5-hydroxymethyl-2-nitro-3-phenylbenzofuran. Recrystallization from an isopropanol-water mixture provides yellow platelets, m.p. 143°–147° C.

| Analysis: | % C | % H | % N |
| --- | --- | --- | --- |
| Calculated for $C_{15}H_{11}NO_4$: | 66.9; | 4.1; | 5.2 |
| Found: | 66.4; | 4.2; | 4.8. |

EXAMPLE 15

A stirred mixture of 2.7 g. (0.010 mole) of 2-nitro-3-phenylbenzofuran-7-aldehyde and 20 ml. of diethyl ether is treated with 1.6 g. (0.015 mole) of sodium bisulfite in 10 ml. of water. After 30 minutes, 30 ml. of chloroform is added followed by 1.5 g. (0.030 mole) of sodium cyanide in 5 ml. of water after an additional 30 minutes. About 0.7 g. of sodium bisulfite is added 1.5 hours later, and the mixture is cooled to 0° C. 30 minutes after the bisulfite addition and maintained for about 16 hours. The organic layer is separated, washed with aqueous sodium bisulfite solution, then with water, and dried over magnesium sulfate. Evaporation of the solution provides a solid which is recrystallized from a chloroform-heptane mixture to provide yellow crystals of α-hydroxy-2-nitro-3-phenylbenzofuran-7-acetonitrile, m.p. 137°–139° C.

| Analysis: | % C | % H | % N |
| --- | --- | --- | --- |
| Calculated for $C_{16}H_{10}N_2O_4$: | 65.3; | 3.4; | 9.5 |
| Found: | 64.9; | 3.3; | 9.5. |

EXAMPLE 16

A mixture of 5.0 g. (0.015 mole) of 5-bromomethyl-2-nitro-3-phenylbenzofuran (described in Example 19 of Belgian Pat. No. 846,502) and 1.1 g. (0.015 mole) of thiourea in 200 ml. of ethanol under nitrogen is heated to its reflux temperature for 18 hours, then evaporated to dryness. This residue is dissolved in 50 ml. of glyme, then 300 ml. of 3N hydrochloric acid is added. The residue is separated by filtration and dissolved in 1.6 liters of hot water. Concentrated hydrochloric acid (200 ml.) is added, and the mixture is cooled. The solid is collected by filtration, recrystallized from an ethanol-diethyl ether mixture, dissolved in hot water and filtered to remove solid impurities. Hydrochloric acid (6N) is added dropwise to the solution and the yellow solid product is separated by filtration and dried. The product is 5-amidinothiomethyl-2-nitro-3-phenylbenzofuran hydrochloride hydrate, m.p. 120°–125° C.

| Analysis: | % C | % H | % N |
| --- | --- | --- | --- |
| Calculated for $C_{16}H_{14}ClN_3O_3S \cdot \frac{1}{2} H_2O$: | 51.5; | 4.1; | 11.3 |
| Found: | 51.5; | 4.3; | 11.5. |

EXAMPLE 17

A mixture of 1.4 g. (0.050 mole) of 5-(2-hydroxyethyl)-2-nitro-3-phenylbenzofuran and 0.5 g. (0.065 mole) of acetyl chloride in 20 ml. of pyridine is gradually warmed to 65° C., maintained at 65° C. for 15 minutes then poured into water. The mixture is extracted with diethyl ether, the extracts are washed twice with water, twice with 5 percent hydrochloric acid, twice again with water, twice with sodium bicarbonate solution, twice again with water, once with saturated sodium chloride solution and dried. Evaporation provides a residue which is recrystallized twice from cyclohexane to provide 2-(2-nitro-3-phenyl-5-benzofuran)ethyl acetate, m.p. 94°–95° C.

| Analysis: | % C | % H | % N |
| --- | --- | --- | --- |
| Calculated for $C_{18}H_{15}NO_5$: | 66.5; | 4.6; | 4.3 |
| Found: | 65.7; | 4.4; | 4.1. |

EXAMPLE 18

To a stirred mixture of 1.4 g. of sodium hydride in 150 ml. of ethanol is added 6 ml. of methyl mercaptan, then 6.6 g. (0.02 mole) of 5-bromomethyl-2-nitro-3-phenylbenzofuran. After four hours the mixture is poured into cold water, this mixture is extracted with diethyl ether, the extracts are washed with 5 percent sodium hydroxide solution, water and saturated sodium chloride solution, then dried. Evaporation provides yellow 5-methylthiomethyl-2-nitro-3-phenylbenzofuran. The structural assignment is supported by infrared spectral analysis.

EXAMPLE 19

A solution of 2.8 g. (0.009 mole) of 5-methylthiomethyl-2-nitro-3-phenylbenzofuran in 200 ml. of acetic acid is obtained by warming. The solution is cooled to 20° C., and 0.51 g. (0.0045 mole) of hydrogen peroxide in 15 ml. of acetic acid is added dropwise. After 20 hours, an additional 1.02 g. of 30 percent hydrogen peroxide in 20 ml. of acetic acid is added dropwise. After an additional 2.5 hours, the reaction is poured onto ice, the precipitate is collected by filtration and washed with water, then dissolved in a dichloromethane-diethyl ether mixture. This mixture is washed with water and saturated sodium chloride solution, then dried. Evaporation provides a solid which is dissolved in chloroform and eluted through a silica gel column with more chloroform. The desired product is eluted from the silica gel with ethyl acetate, recrystallized from a benzene-hexane mixture then from aqueous ethanol to provide yellow plates of 5-methylsulfinylmethyl-2-nitro-3-phenylbenzofuran, m.p. 162°–165° C.

| Analysis: | % C | % H | % N |
| --- | --- | --- | --- |
| Calculated for $C_{16}H_{13}NO_4S$: | 60.94; | 4.16; | 4.44 |

| Analysis: | % C | % H | % N |
|---|---|---|---|
| Found: | 60.8; | 4.2; | 4.4. |

EXAMPLE 20

A mixture of 2.8 g. (0.009 mole) of 5-methylthiomethyl-2-nitro-3-phenylbenzofuran and 160 ml. of acetic acid is heated to 40° C., and 2.0 g. (0.018 mole) of hydrogen peroxide in 30 ml. of acetic acid is added dropwise as the temperature rises to 50° C. The solution is stirred for about six hours at 50° C. and for about 16 hours at 20° C., then poured into cold water. The precipitate is collected by filtration, rinsed with water and dissolved in dichloromethane. The solution is washed with water and saturated sodium chloride solution, then dried. Evaporation provides yellow solid which is recrystallized from a benzene-hexane mixture to give 5-methylsulfonylmethyl-2-nitro-3-phenylbenzofuran, m.p. 178°–181° C.

| Analysis: | % C | % H | % N |
|---|---|---|---|
| Calculated for $C_{16}H_{13}NO_5S$: | 58.0; | 4.0; | 4.2 |
| Found: | 58.2; | 4.1; | 4.3. |

EXAMPLE 21

A mixture of 16 ml. of dimethyl sulfide and 25 g. (0.068 mole) of 2-bromo-5-bromomethyl-3-phenylbenzofuran (described in Example 19 of Belgian Patent 846,502) in 250 ml. of acetic acid is warmed to 50° C., and 9.5 g. (0.103 mole) of dinitrogen tetraoxide in 40 ml. of acetic acid is added dropwise at 50° to 55° C. An additional 16 ml. of dimethyl sulfide is added. The solid precipitate is separated by filtration and recrystallized from methanol to provide yellow needles of 2-nitro-3-phenylbenzofuran-5-dimethylsulfoniummethyl bromide, m.p. 190° C. (dec.).

| Analysis: | % C | % H | % N |
|---|---|---|---|
| Calculated for $C_{16}H_{13}NO_3S \cdot CH_3Br$: | 51.8; | 4.1; | 3.5 |
| Found: | 51.5; | 3.9; | 3.6. |

EXAMPLE 22

Step A. To a stirred, cold solution of 7.8 g. of 2-bromo-5-methylthiomethyl-3-phenylbenzofuran (prepared by reacting 2-bromo-5-bromomethyl-3-phenylbenzofuran with methyl mercaptan according to the procedure of Example 18 hereof) in 100 ml. of chloroform is added dropwise 4.73 g. of 3-chloroperbenzoic acid in chloroform at 0° C. After three hours an addition 0.3 g. of the peracid is added and 30 minutes later the solution is washed with cold 5 percent sodium hydroxide solution, then with saturated sodium chloride solution and dried. Evaporation provides a residue which is recrystallized from a chloroform-hexane mixture to provide 2-bromo-5-methylsulfinylmethyl-3-phenylbenzofuran. The structural assignment is confirmed by infrared and nuclear magnetic resonance spectral analysis.

Step B. The product of step A is dissolved in 100 ml. of acetic acid, 3.3 g. of itaconic acid is added followed by 2.3 g. of dinitrogen tetraoxide in 10 ml. of acetic acid (the latter being added dropwise). After two hours, the mixture is poured into water and extracted with diethyl ether. The ether extracts are washed with dilute sodium bicarbonate solution, with saturated sodium chloride solution, then dried. Evaporation provides a solid which is dissolved in chloroform and chromatographically fractionated on silica gel, eluting with chloroform-carbon tetrachloride, then chloroform. The desired product elutes slowly with chloroform. It is washed with hot hexane, then recrystallized from a hexane-chloroform mixture to provide 5-methylsulfinylmethyl-2-nitro-3-phenylbenzofuran, m.p. 161°–163° C. This is the product of Example 19.

EXAMPLE 23

To a stirred mixture of 2.2 g. (0.0022 mole) of 2-bromo-5-methylthiomethyl-3-phenylbenzofuran and 1.0 g. (0.0077 mole) of itaconic acid in 40 ml. of acetic acid is added 4.0 g. (0.0043 mole) of dinitrogen tetraoxide in 15 ml. of acetic acid. After about 16 hours the mixture is poured into water and the resulting solid is separated by filtration. It is then dissolved in diethyl ether, washed with saturated sodium bicarbonate solution, saturated sodium chloride solution and dried. Evaporation provides a residue which is recrystallized from a chloroform-hexane mixture to provide 5-(2-nitro-3-phenylbenzofuranyl)methyl acetate, m.p. 110°–112° C.

| Analysis: | % C | % H | % N |
|---|---|---|---|
| Calculated for $C_{17}H_{13}NO_5$: | 65.6; | 4.2; | 4.5 |
| Found: | 65.5; | 4.2; | 4.6. |

EXAMPLE 24

Step A. A mixture of 54.9 g. (0.15 mole) of 2-bromo-5-bromomethyl-3-phenylbenzofuran and 11.5 g. (0.15 mole) of thiourea in 250 ml. of ethanol is heated at its reflux temperature for about 5.5 hours. The solution is diluted with 400 ml. of diethyl ether. A solid precipitates and is collected by filtration, then suspended in 400 ml. of ethanol. To this suspension is added 50 ml. of 10 percent sodium hydroxide solution. After stirring for 30 minutes, 100 ml. of 6N hydrochloric acid and 500 ml. of water are added. The solid product 2-bromo-5-mercaptomethyl-3-phenylbenzofuran is collected by filtration.

Step B. The product of step A is dissolved in 600 ml. of acetic acid and 25 ml. of water, the product is cooled to 10° C. and 500 ml. of acetic acid saturated with chlorine is added. Additional chlorine is bubbled in over two hours, and the solution is stirred an additional two hours, then 300 ml. of water are added. The solid is collected, dissolved in chloroform and dried. The solvent is evaporated, hexane is added and the solid product, 2-bromo-5-chlorosulfonylmethyl-3-phenylbenzofuran is precipitated and separated by filtration.

Step C. The product of step B is dissolved in 50 ml. of dichloromethane, 0.8 g. of cyclohexane and 0.9 g. of dinitrogen tetraoxide is added, and the mixture is stirred for about 16 hours. Evaporation provides a residue which is dissolved in dichloromethane, and ammonia gas is bubbled into the solution. After stirring for two hours, the solution is washed with dilute hydrochloric acid, saturated sodium chloride solution and then dried. Evaporation provides a residue which is recrystallized thrice from ethanol to yield yellow solid 2-nitro-3-phenylbenzofuran-5-methanesulfonamide, m.p. 203°–205° C.

| Analysis: | % C | % H | % N |
| --- | --- | --- | --- |
| Calculated for $C_{15}H_{12}N_2O_5S$: | 54.2; | 3.64; | 8.43 |
| Found: | 54.1; | 3.6; | 8.0. |

EXAMPLE 25

Using the method of Example 24, step C, 2-bromo-5-chlorosulfonylmethyl-3-phenylbenzofuran is nitrated, then reacted with methylamine to provide N-methyl-2-nitro-3-phenylbenzofuran-5-methanesulfonamide.

EXAMPLE 26

Using the method of Example 24, step C, 2-bromo-5-chlorosulfonylmethyl-3-phenylbenzofuran is nitrated, then reacted with pyrrolidine to provide N-[5-(2-nitro-3-phenylbenzofuran)methylsulfonyl]pyrrolidide.

EXAMPLE 27

Step A. A mixture of 40 g. of 4-methylphenol, 100 g. of 4-bromo-α-bromoacetophenone and 80 g. of potassium carbonate in 1 liter of acetone is heated to its reflux temperature and maintained at reflux with stirring for 64 hours. To this mixture is added 10 g. of potassium carbonate and refluxing is continued for an additional five hours more. The mixture is cooled, filtered and evaporated to provide a residue of α-(4-methylphenoxy)-4-bromoacetophenone as light brown crystals after recrystallization from aqueous isopropanol.

Step B. The product of step A is mixed with 500 g. of polyphosphoric acid and heated at 100° C. for two hours with stirring. The mixture is decanted into 1 liter of ice water, the aqueous mixture is extracted with diethyl ether, and the ether extracts are washed with saturated sodium chloride solution and dried. The solution is evaporated to provide a brown oil which is distilled at 160°–170° C. at 0.25 mm. Hg to provide 3-(4-bromophenyl)-5-methylbenzofuran.

Step C. The product of step B in 150 ml. of tetrahydrofuran is added to 5 g. of magnesium turnings in 25 ml. of tetrahydrofuran at a rate sufficient to sustain refluxing. Refluxing is continued for an additional three hours, then the mixture is stirred overnight at about 20° C. To this reaction mixture is added gaseous carbon dioxide over a period of one hour. The mixture is maintained at reflux during the second half hour. The reaction mixture is cooled and cautiously added to 50 ml. of 6N hydrochloric acid. The reaction mixture is evaporated to provide a residue which is recrystallized from acetic acid to provide tan crystals of 3-(5-methyl-3-benzofuranyl)benzoic acid.

Step D. A solution of 22.5 g. of the product of step C and 2 g. of cupric nitrate in 100 ml. of acetonitrile is cooled with an ice bath, and 10 g. of dinitrogen tetraoxide in 20 ml. of acetonitrile is added over a period of 10 minutes. The ice bath is removed, and the mixture is stirred at 20° C. for four hours. The mixture is then evaporated, partially cooled and filtered. The residue is recrystallized from aqueous N,N-dimethylformamide. The product is yellow crystals of 4-(5-methyl-2-nitro-3-benzofuranyl)benzoic acid, m.p. 258° C. (dec.).

| Analysis: | % C | % H | % N |
| --- | --- | --- | --- |
| Calculated for $C_{16}H_{11}NO_5$: | 64.6; | 3.7; | 4.7 |
| Found: | 64.2; | 3.7; | 4.8. |

Step E. To a solution of the product of step D in 200 ml. of tetrahydrofuran is added 150 ml. of 1N diborane in tetrahydrofuran. The mixture is heated to its reflux temperature and is maintained at reflux for two hours. To this solution is added 100 ml. of 3N sulfuric acid. This mixture is heated to its reflux temperature and maintained at reflux for about one hour, then evaporated to provide a residue. The residue is recrystallized from aqueous isopropanol to provide yellow crystals of 3-(4-hydroxymethyl)phenyl-5-methyl-2-nitrobenzofuran, m.p. 145°–147° C.

| Analysis: | % C | % H | % N |
| --- | --- | --- | --- |
| Calculated for $C_{16}H_{13}NO_4$: | 67.8; | 4.6; | 4.9 |
| Found: | 67.4; | 4.6; | 4.7. |

EXAMPLE 28

Using the method of Example 13 and starting with 3-(4-hydroxymethylphenyl)-2-nitrobenzofuran the intermediate compound 3-(4-bromomethylphenyl)-2-nitrobenzofuran is prepared. Using the method of Example 18 this intermediate is converted to 2-(4-methylthiomethylphenyl)-2-nitrobenzofuran.

What is claimed is:

1. A compound of the formula

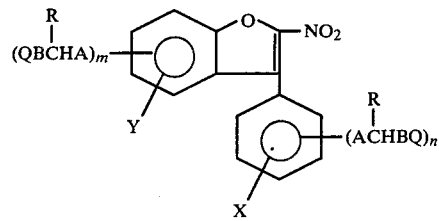

wherein

A is a carbon-carbon bond, methylene,

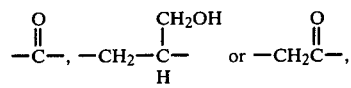

R is hydrogen, alkyl of one to ten carbon atoms or cyano,

B is oxygen, sulfur, sulfinyl or sulfonyl,

Q is hydrogen, amino, methylamino, N-bonded pyrrolidinyl, alkyl of one to four carbon atoms,

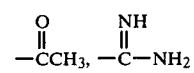

or nitroso, m and n are independently zero or one and the sum of m and n is one or two, X is hydrogen, methyl, fluorine, chlorine and bromine and Y is hydrogen, methyl or ethyl, provided that when Q is amino, methylamino or pyrrolidinyl, B and R in the same moiety are respectively sulfonyl and hydrogen.

2. A compound according to claim 1 wherein Q contains zero, one or two carbon atoms.

3. A compound according to claim 1 wherein B is oxygen.

4. A compound according to claim 3 wherein Q is hydrogen, alkyl of one to four carbon atoms,

or nitroso.

5. A compound according to claim 4 wherein R is cyano and Q is hydrogen.

6. A compound according to claim 4 wherein R is hydrogen.

7. A compound according to claim 3 wherein n is zero and m is one.

8. A compound according to claim 6 wherein n is zero and m is one.

9. A compound according to claim 3 wherein Q contains zero, one or two carbon atoms.

10. A compound according to claim 8 wherein R and Q are hydrogen, B is oxygen and A is

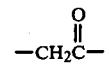

or -carbonyl.

11. A compound according to claim 1 wherein X and R are both hydrogen.

12. A compound according to claim 1 wherein B is sulfur, sulfinyl or sulfonyl and R is hydrogen.

13. A compound according to claim 12 wherein Q is hydrogen, amino alkyl of one to ten carbon atoms or

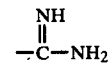

14. A method for arresting or inhibiting the growth of microorganisms comprising contacting microorganisms with a compound according to claim 1 in an amount sufficient to inhibit the growth of said microorganisms.

15. The compound 2-nitro-3-phenylbenzofuran-5-dimethylsulfoniummethyl bromide.

* * * * *